United States Patent
Chen et al.

(10) Patent No.: US 10,752,568 B1
(45) Date of Patent: Aug. 25, 2020

(54) METHOD FOR PREPARING 1,3-PROPANEDIOL BY HYDROGENOLYSIS OF GLYCEROL AND ITS REACTION SYSTEM

(71) Applicant: Zhangjiagang Glory Chemical Industry Co., Ltd., Jiangsu Province (CN)

(72) Inventors: Changlin Chen, Jiangsu Province (CN); Xiaodong Zhu, Jiangsu Province (CN); Bing Han, Jiangsu Province (CN); Chengchao Xiao, Jiangsu Province (CN)

(73) Assignee: Zhangjiagang Glory Chemical Industry Co., Ltd., Jiangsu Province (CN)

( * ) Notice: Subject to any disclaimer, the term of this patent is extended or adjusted under 35 U.S.C. 154(b) by 0 days.

(21) Appl. No.: 16/443,213

(22) Filed: Jun. 17, 2019

(51) Int. Cl.
  *C07C 29/60* (2006.01)
  *B01J 23/652* (2006.01)
  *C07C 31/20* (2006.01)
  *B01J 23/38* (2006.01)

(52) U.S. Cl.
  CPC .............. *C07C 29/60* (2013.01); *B01J 23/38* (2013.01); *B01J 23/6527* (2013.01); *C07C 31/205* (2013.01)

(58) Field of Classification Search
  CPC ........ C07C 29/60; C07C 31/205; B01J 23/38; B01J 23/40; B01J 23/42; B01J 23/43; B01J 23/46; B01J 23/48; B01J 23/54
  See application file for complete search history.

(56) References Cited

U.S. PATENT DOCUMENTS

| | | | |
|---|---|---|---|
| 6,080,989 A | 6/2000 | Drent et al. | |
| 7,663,004 B2 * | 2/2010 | Suppes | C07C 29/145 568/862 |
| 8,563,783 B2 * | 10/2013 | Suppes | C07C 45/52 568/861 |
| 2009/0177018 A1 | 7/2009 | Suzuki et al. | |
| 2011/0160482 A1 | 6/2011 | Nagaki et al. | |

FOREIGN PATENT DOCUMENTS

| | | | |
|---|---|---|---|
| CN | 1264356 A | 8/2000 | |
| CN | 101747150 A | 6/2010 | |
| CN | 102344341 A | 2/2012 | |
| CN | 102728380 A | 10/2012 | |
| CN | 109608307 | * 4/2019 | ............. C07C 29/60 |

OTHER PUBLICATIONS

CN 109608307, Chen Changlin et al., Method and reaction system for preparing 1,3-propanediol by hydrogenolysis of glycerol, English traslation, 12 pages (Year: 2019).*
Dasari, M. A., et al., Low-pressure hydrogenolysis of glycerol to propylene glycol, 2005, Applied Catalysis A: General, vol. 281, pp. 225-231 (Year: 2005).*
Arundhathi, R., et al., Highly selective hydrogenolysis of glycerol to 1,3-propanediol over a Boehmite-supported Platinum/Tungsten catalyst, 2013, ChemSusChem Communications, vol. 6, pp. 1345-1347 (Year: 2013).*
Li, K-T, et al., Aqueous-phase hydrogenolysis of glycerol over Re promoted Ru catalyst encapuslated in porous silica nanoparticles, 2018, Nanomaterials, vol. 8, No. 153, 14 pages (Year: 2018).*
Leifeng, G. et al., Solvent effect on selective dehydroxylationof glycerol to 1,3-propanediol over a Pt/WO3/ZrO3 catalyst, 2009, Chinese Journal of Catalysis, vol. 30, issue 12, pp. 1189-1191 (3 pages available from Science Direct) (Year: 2009).*
Mizugaki, T., et al., Selective hydrogenolysis of gycerol to 1,3-propanediol catalyzed by Pt nanoparticles-AlOx/WO3, Chemistry Letters, vol. 41, pp. 1720-1722 (Year: 2012).*
Solvent Effect on Selective Dehydroxylation of Glycerol to 1,3-propanediol over a Pt/W03/Zr02 Catalyst, Chinese Journal of Catalysis, vol. 30, No. 12 Dec. 2009.

* cited by examiner

*Primary Examiner* — Yate' K Cutliff
(74) *Attorney, Agent, or Firm* — Meunier Carlin & Curfman LLC

(57) ABSTRACT

The present disclosure provides a method for preparing 1,3-propanediol by hydrolysis hydrogenolysis of glycerol and its corresponding reaction system, wherein, this method is to produce 1,3-propanediol through contact and reaction between hydrogen and glycerol under the catalysis of a noble metal/solid acid catalyst; wherein an auxiliary agent is contained in the liquid phase of the reaction system, and the content of the auxiliary agent in the liquid phase is 10 ppm or more.

17 Claims, No Drawings

METHOD FOR PREPARING 1,3-PROPANEDIOL BY HYDROGENOLYSIS OF GLYCEROL AND ITS REACTION SYSTEM

TECHNICAL FIELD

The present disclosure belongs to the technical field of chemical engineering; specifically, relates to a method for preparing 1,3-propanediol by hydrogenolysis of glycerol and its reaction system.

BACKGROUND 1,3-propanediol, which is an important raw material in fine chemical industry, can be used in inks, printing and dyeing, drugs, lubricants, antifreeze agents, as well as diols for the synthesis of heterocycles, pharmaceutical intermediates, etc. Currently, the most important use of 1,3-propanediol is as a polymer monomer to synthesize degradable polyester trimethylene terephthalate (PTT). PTT has both the high-strength and stability of PET (polyethylene terephthalate) and the excellent molding processing property of PBT (polybutylene terephthalate); moreover, PTT is comparable to PA6 and PA66 in elastic recovery, showing soft and excellent drapability, good quality touch and comfortable elasticity. Additionally, PTT also has good anti-fouling and wear resistance. Therefore, PTT has been used in some fields such as fibers for clothing, low carbon materials and engineering plastics with a huge potential market. For example in the textile field, since PTT fiber has excellent flexibility and elastic recovery, good wrinkle resistance and dimensional stability, good weather resistance and dyeing performance, and good barrier performance so as to withstand γ-ray disinfection, clothing made of such fiber is comfortable in dress, soft in touch, easy to wash, quick to dry, and free of ironing. It is apparent that PTT fiber fabric has a great market potential. With the huge demand for PTT in the industrial field, 1,3-propanediol which is used as the raw material for the synthesis of PTT is bound to promote its development. At present, the large-scale application of PTT is limited mainly due to the price of 1,3-propanediol. Therefore, it is of great significance to develop a synthesis process of 1,3-propanediol with low cost.

At present, it is considered that a process route, in which glycerol used as the raw material is hydrogenated to produce 1,3-propanediol, is promising. A metal/solid acid bifunctional catalyst is generally used in this process, and the reaction is carried out in aqueous medium. However, this process has an apparent defect in that the catalyst is easily deactivated and has a poor stability. So far, there is no good solution yet, and thus this defect is still an important factor that hinders the industrial application of this process.

SUMMARY

To solve the above-mentioned technical problem, the present disclosure is aimed to provide a method for preparing 1,3-propanediol by hydrogenolysis of glycerol.

Another purpose of the present disclosure is to provide a reaction system for preparing 1,3-propanediol by hydrogenolysis of glycerol.

In order to achieve the above purpose, provided herein is a method for preparing 1,3-propanediol by hydrogenolysis of glycerol, wherein this method is to produce 1,3-propanediol through contact and reaction between hydrogen and glycerol under the catalysis of a noble metal/solid acid catalyst; wherein an auxiliary agent is contained in the liquid phase of the reaction system; wherein the auxiliary agent is alkali metal phosphate; and the content of the auxiliary agent in the liquid phase is 10 ppm or more.

In a conventional reaction system in which 1,3-propanediol is prepared though hydrogenolysis of glycerol, the noble metal/solid acid catalyst as used generally has poor stability; with the progress of the reaction, the activity of the catalyst decreases, and moreover such activity is significantly decreased when the reaction has not operated for a long time. By intensive study, the applicant has found that the reason for which the catalyst is easily deactivated in this reaction system is mainly due to two aspects: on one hand, the activity of the catalyst is decreased because of chemical transformation or crystal structure transformation of the acid oxide; on the other hand, the decrease in activity results from such factors as loss or aggregation of active metal. Therefore, the stability of the catalyst can be substantially improved only by comprehensive treatment of the two aspects mentioned above. It is found in further research that when a certain concentration of an alkali metal phosphate is maintained in the liquid phase of the reaction system, it can not only effectively reduce the chemical transformation and crystal phase transformation of the acid oxide, but also enhance the binding force of active metal to carrier. Additionally, since such an auxiliary agent is beneficial to the stability of $H^+$ and $H^-$ formed by heterolytic activation of hydrogen, it can improve the conversion of glycerol and the selectivity of 1,3-propanediol to a certain extent during the hydrogenation of glycerol. The concentration of the auxiliary agent contained in the liquid phase has an important effect on the long-term stability of the catalyst. Research shows that the concentration of the auxiliary agent should not be too low, which especially has an effect on improving the binding force of active metal to carrier; thus, the concentration is generally more than 10 ppm. In addition, the concentration does not have to be too high, and those skilled in the art can adjust it according to actual situation under the basic condition for maintaining the reaction system. The test results show that the enhancement of the catalyst stability tends to flatten out when the concentration of the catalyst is increased to a certain degree; accordingly, it is recommended that the concentration is 600 ppm or less.

In the method for preparing 1,3-propanediol by hydrogenolysis of glycerol as mentioned above, "liquid phase" refers to a mixture of all liquid-phase substances in an entire reaction system (generally referred to as a gas-liquid-solid three-phase system formed during a contact and reaction; referred to as a liquid-solid two-phase system formed during a liquid-liquid contact and reaction). Under conventional conditions, when the reaction is carried out, in addition to unreacted glycerol and solvent, the liquid-phase substances in the system include all the substances in liquid form generated by the reaction, for example, 1,3-propanediol, 1,2-propanediol, n-propanol, isopropanol, generated water and other products.

In some embodiments of the method for preparing 1,3-propanediol by hydrogenolysis of glycerol as mentioned above, the alkali metal phosphate can be selected from alkaline metal orthophosphate, pyrophosphate, metaphosphate, dihydrogen phosphate or monohydrogen phosphate. In some embodiments, the alkali metal phosphate is selected from one or a combination of several types of sodium phosphate, potassium phosphate, rubidium phosphate, cesium phosphate, lithium phosphate, and lithium dihydrogen phosphate. In some embodiments, the alkali metal phosphate includes one or a combination of several types of rubidium phosphate, cesium phosphate, lithium phosphate, and lithium dihydrogen phosphate.

In some embodiments of the method for preparing 1,3-propanediol by hydrogenolysis of glycerol as mentioned above, the content of the auxiliary agent in the liquid phase of the reaction system is from 50 ppm to 400 ppm or from 80 ppm to 300 ppm.

In some embodiments of the method for preparing 1,3-propanediol by hydrogenolysis of glycerol as mentioned above, the auxiliary agent and the raw material (hydrogen, glycerol) or solvent can be fed into the reactor after mixing, or alternatively the auxiliary agent can be directly added into the liquid phase in the reactor, as long as the auxiliary agent contained in the liquid phase is 10 ppm or more.

In some embodiments of the method for preparing 1,3-propanediol by hydrogenolysis of glycerol as mentioned above, after continuous contact and reaction between hydrogen and glycerol under the catalysis of noble metal/solid acid catalyst in a fixed-bed reactor, a mixture formed of 1,3-propanediol, by-product (1,2-propanediol. n-propanol, isopropanol, water and other products), unreacted glycerol and solvent is continuously discharged from the outlet of the fixed-bed reactor, and the amount of the auxiliary agent added to the feed of glycerol or solvent is controlled such that the content of the auxiliary agent contained in the mixture which is discharged from the outlet of the fixed-bed reactor is maintained at 10 ppm or more, from 50 ppm to 400 ppm, or from 80 ppm to 300 ppm.

In some embodiments of the method for preparing 1,3-propanediol by hydrogenolysis of glycerol as mentioned above, a one-step method which is common in the art can be used for preparing the noble metal/solid acid catalyst for the synthesis of 1,3-propanediol. In some embodiments, the noble metal is one or a combination of several types of platinum, palladium, rhodium, iridium, and ruthenium; the solid acid is one or a combination of several types of $ZrO_2$, $WO_3$, $MoO_3$, $Al_2O_3$, $TiO_2$ and $SiO_2$. Each component in the catalyst can be contained in a regular amount. In some embodiments, the content of the noble metal is 0.5-3% by weight, and the rest is solid acid.

In some embodiments of the method for preparing 1,3-propanediol by hydrogenolysis of glycerol as mentioned above, the noble metal/solid acid catalyst is Pt—$WO_3$—$ZrO_2$ or Pt—$WO_3$—$Al_2O_3$.

In some embodiments of the method for preparing 1,3-propanediol by hydrogenolysis of glycerol as mentioned above, the conditions for the reaction can be set normally. In some embodiments, the conditions of contact and reaction are as follows: the reaction temperature is 130-190° C. and reaction pressure is 1-25 MPa.

In some embodiments of the method for preparing 1,3-propanediol by hydrogenolysis of glycerol as mentioned above, the solvent in the reaction system can be a conventional solvent in the art, for example, water, n-propanol, isopropanol, ethanol or dimethyl sulfoxide (and glycerol itself acts as a solvent as well). In some embodiments, the solvent is water.

In some embodiments of the method for preparing 1,3-propanediol by hydrogenolysis of glycerol as mentioned above, the amount and the ratio of the main reactants (hydrogen and glycerol) can be set according to the conventional reaction. In some embodiments, the molar ratio of hydrogen to glycerol into the reaction system is 1-20:1.

In some embodiments, the glycerol and water are added into the reactor in the form of an aqueous glycerol solution when the solvent is water, and the aqueous glycerol solution has a mass concentration of 20-90% by weight.

The present disclosure also provides a reaction system for preparing 1,3-propanediol by hydrogenolysis of glycerol as used in the above method. The concentration of the auxiliary agent is 10 ppm or more in the liquid phase of this reaction system. As for the liquid phase (reaction solution) drawn from the reactor at the end of reaction, the product is separated while the auxiliary agent can be recovered, and the recovered auxiliary agent can be re-introduced into the reaction system after proper treatment.

By adding the auxiliary agent into the liquid phase of the reaction system, the stability of the noble metal/solid acid catalyst can be significantly increased, and the activity of the catalyst and the selectivity for 1,3-propanediol can be enhanced to a certain degree.

The details of one or more embodiments of the disclosure are set forth in the description below. Other features, objects, and advantages of the disclosure will be apparent from the description, and from the claims.

DETAILED DESCRIPTION

A number of embodiments of the disclosure have been described. Nevertheless, it will be understood that various modifications may be made without departing from the spirit and scope of the present disclosure. Accordingly, other embodiments are within the scope of the following claims.

By way of non-limiting illustration, examples of certain embodiments of the present disclosure are given below.

The technical solutions of the invention shall be now described in detail as follows in order to have a clearer understanding of the technical features, purposes and beneficial effects of the invention, but it should not be understood as limiting of the implementable range of the invention.

Example 1

The present example provided a method for preparing 1,3-propanediol by hydrogenolysis of glycerol (the auxiliary agent was added into the aqueous glycerol solution), in which the catalyst as used was Pt—$WO_3$—$ZrO_2$ (the content of Pt was 2.0% by weight; the content of $WO_3$ was 30% by weight, and rest was $ZrO_2$) prepared by the conventional method. This method included the following steps:

(1) The catalyst was placed at a position which is 30 cm from the bottom of the reactor (a tube typed fixed-bed reactor has a diameter of 1 cm and a length of 1 m), the loaded volume of catalyst is 5 mL, wherein the particle of the catalyst is in a form of sphere with a particle size of 0.5-1.0 mm, and the rest was filled with inert alumina ball;

(2) Hydrogen was continuously fed into the catalyst at 250° C. for 1 hour to activate the catalyst;

(3) The aqueous glycerol solution was injected into the reactor with the rate of 0.3 $h^{-1}$ (this solution contained glycerol with the mass content of 60% by weight and included the auxiliary agent), and meanwhile hydrogen was injected into the reactor with a rate of 150 ml/min; the ratio of hydrogen to glycerol was 2000; the reaction conditions were as follows: reaction temperature was 150° C. and reaction pressure was 6 MPa; the reaction was carried out for 3000 hours. During the reaction, samples were taken out for analysis by chromatography. The analytic results are shown in Table 1.

TABLE 1 test results of catalyst stability by adding different auxiliary agents into the liquid phase

| the added auxiliary agent | reaction for 48 hours | | reaction for 100 hours | | reaction for 300 hours | | reaction for 1000 hours | | reaction for 3000 hours | |
|---|---|---|---|---|---|---|---|---|---|---|
| | conversion (%) | selectivity (%) | conversion (%) | selectivity (%) | conversion (%) | selectivity (%) | conversion (%) | selectivity (%) | conversion (%) | selectivity (%) |
| $Li_3PO_4$ 10 ppm | 54.8 | 50.1 | 49.2 | 51.1 | 43.1 | 51.4 | 36.8 | 49.9 | 29.3 | 52.5 |
| $Li_3PO_4$ 50 ppm | 58.1 | 53.2 | 56.6 | 53.2 | 48.9 | 54.2 | 44.7 | 54.7 | 39.2 | 55.3 |
| $Li_3PO_4$ 100 ppm | 60.2 | 55.2 | 59.3 | 57.1 | 58.6 | 58.2 | 58.2 | 58.8 | 58.2 | 59.1 |
| $Li_3PO_4$ 300 ppm | 62.3 | 54.6 | 58.2 | 56.2 | 53.1 | 57.4 | 51.6 | 56.3 | 49.5 | 57.1 |
| $Na_3PO_4$ 100 ppm | 50.3 | 47.8 | 48.4 | 48.3 | 43.2 | 49.2 | 35.9 | 48.2 | 26.3 | 48.3 |
| $K_3PO_4$ 100 ppm | 53.7 | 49.3 | 49.8 | 50.4 | 47.2 | 51.3 | 39.0 | 52.2 | 24.3 | 51.7 |
| $Rb_3PO_4$ 100 ppm | 56.2 | 57.3 | 50.1 | 58.3 | 51.3 | 57.1 | 50.2 | 58.2 | 50.2 | 58.2 |
| $Cs_3PO_4$ 100 ppm | 58.2 | 52.1 | 52.1 | 54.1 | 56.8 | 57.1 | 55.6 | 57.2 | 51.2 | 57.7 |
| $Cs_3PO_4$ 400 ppm | 53.1 | 59.1 | 56.1 | 57.9 | 56.9 | 56.3 | 48.3 | 57.5 | 41.6 | 58.5 |

Note: conversion is the conversion of glycerol; selectivity=molar number of 1,3-propanediol/molar number of converted glycerol.

It can be shown from the above test data that the stability of the catalyst can be greatly improved by adding the auxiliary agent into the liquid phase.

Example 2

The present example provided a method for preparing 1,3-propanediol by hydrogenolysis of glycerol (auxiliary agent $Li_3PO_4$ of 100 ppm was added into the aqueous glycerol solution; in addition, a control test was provided without the auxiliary agent). The catalysts were used in this method as follows:

M1: Pt—$WO_3$—$Al_2O_3$ (the content of Pt was 2.0% by weight; the content of $WO_3$ was 34% by weight, and the rest was $Al_2O_3$);

M2: Ir—$SiO_2$—$TiO_2$ (the content of Ir was 2.0% by weight; the content of $SiO_2$ was 35% by weight, and the rest was $TiO_2$);

M3: Pb—$MoO_3$—$Al_2O_3$ (the content of Pb was 2.0% by weight; the content of $SiO_2$ was 30% by weight, and the rest was $Al_2O_3$);

During the reaction, the sample was taken out for analysis by chromatography. The analytic results are shown in Table 2.

TABLE 2

Test results on stability under different systems

| Catalyst and auxiliary | reaction for 48 hours | | reaction for 100 hours | | reaction for 300 hours | | reaction for 1000 hours | | reaction for 3000 hours | |
|---|---|---|---|---|---|---|---|---|---|---|
| | conversion (%) | selectivity (%) | conversion (%) | selectivity (%) | conversion (%) | selectivity (%) | conversion (%) | selectivity (%) | conversion (%) | selectivity (%) |
| M1/ $K_3PO_4$ 100 ppm | 40.2 | 60.2 | 37.3 | 60.3 | 37.2 | 61.2 | 36.4 | 61.5 | 36.3 | 61.2 |
| M1 Without auxiliary agent | 36.2 | 57.9 | 30.1 | 56.9 | 25.3 | 57.8 | 17.3 | 57.2 | 12.7 | 58.1 |
| M2/ $Cs_3PO_4$ 100 ppm | 20.1 | 40.1 | 16.2 | 41.2 | 17.9 | 42.1 | 17.8 | 44.2 | 17.9 | 44.6 |
| M2 Without auxiliary agent | 21.2 | 41.1 | 15.2 | 42.6 | 10.7 | 41.1 | 7.8 | 43.2 | 4.9 | 44.6 |
| M3/ $Li_3PO_4$ 100 ppm | 29.2 | 20.3 | 25.1 | 22.1 | 27.4 | 23.0 | 27.2 | 22.3 | 27.3 | 23.1 |
| M3 Without auxiliary agent | 29.8 | 19.3 | 20.2 | 20.7 | 16.7 | 21.6 | 11.8 | 23.3 | 7.3 | 20.9 |

Note: conversion is the conversion of glycerol; selectivity=molar number of 1,3-propanediol/molar number of converted glycerol.

Comparative Example 1

This comparative example provided two comparison experiments as follows: Comparison experiment A was carried out under the same process condition as that in example 1 except that no auxiliary agent was added into the liquid phase;

Comparison experiment B was carried out under the same process condition as that in example 1 except that no auxiliary agent was added into the liquid phase and a different catalyst was used; the catalyst used in this comparison experiment was Pt—$WO_3$—$ZrO_2$ modified by $Li_3PO_4$, which was produced by doping $Li_3PO_4$ during the preparation process of the catalyst in example 1; the content of each component in this catalyst was as follows: the content of Pt was 2.0% by weight, the content of $WO_3$ was 30% by weight, the content of $Li_3PO_4$ was 1.0% by weight, and the rest was $ZrO_2$. Test results are shown in Table 3.

TABLE 3

Test results on stability of catalyst in comparison experiment

| comparison experiment | reaction for 48 hours | | reaction for 100 hours | | reaction for 300 hours | | reaction for 1000 hours | | reaction for 3000 hours | |
|---|---|---|---|---|---|---|---|---|---|---|
| | conversion (%) | selectivity (%) | conversion (%) | selectivity (%) | conversion (%) | selectivity (%) | conversion (%) | selectivity (%) | conversion (%) | selectivity (%) |
| A | 54.2 | 46.2 | 48.3 | 47.3 | 40.1 | 48.1 | 30.2 | 48.3 | 12.2 | 49.1 |
| B | 56.4 | 49.3 | 47.3 | 50.1 | 38.7 | 50.3 | 30.9 | 50.5 | 14.6 | 50.7 |

Note: conversion is the conversion of glycerol; selectivity=molar number of 1,3-propanediol/molar number of converted glycerol.

It can be shown from the test data shown in Tables 1-3 that:

(1) The catalyst still had good activity when the reaction was carried out for 3000 hours by using the process in the present solution. It can be seen that the stability of the catalyst can be significantly improved while this process can increase the conversion and the selectivity of 1,3-propanediol to certain degree.

(2) Compared with the technical solution in which the auxiliary agent is only added into the reaction solution, the technical solution where both the catalyst and the reaction solution contain the auxiliary agent can reduce the decrease of the catalyst activity at initial stage, and thus a better stability can be obtained; moreover, this solution has more remarkable effect on providing the conversion and the selectivity for 1,3-propanediol.

What is claimed is:

1. A method for preparing 1,3-propanediol by hydrogenolysis of glycerol, comprising: contacting and reacting hydrogen and glycerol in a reaction system under a catalysis of a noble metal/solid acid catalyst; wherein an auxiliary agent is contained in a liquid phase of the reaction system; wherein the auxiliary agent is selected from an alkali metal phosphate; and wherein the auxiliary agent in the liquid phase is present in an amount of 10 ppm or more.

2. The method of claim 1, wherein the alkali metal phosphate is selected from sodium phosphate, potassium phosphate, rubidium phosphate, cesium phosphate, lithium phosphate, and lithium dihydrogen phosphate, or a combination thereof.

3. The method of claim 2, wherein, the alkali metal phosphate is selected from rubidium phosphate, cesium phosphate, lithium phosphate, and lithium dihydrogen phosphate, or a combination thereof.

4. The method of claim 1, wherein the auxiliary agent in the liquid phase of the reaction system is present in an amount from 50 ppm to 400 ppm.

5. The method of claim 4, wherein the auxiliary agent in the liquid phase of the reaction system is present in an amount from 80 ppm to 300 ppm.

6. The method of claim 1, further comprising: wherein after a continuous contact and reaction between hydrogen and glycerol under the catalysis of the noble metal/solid acid catalyst in a fixed-bed reactor, continuously discharging a mixture formed of 1,3-propanediol, by-product, unreacted glycerol and solvent from an outlet of the fixed-bed reactor; wherein an amount of the auxiliary agent added to a feed of glycerol or solvent to the fixed-bed reactor is controlled such that the auxiliary agent contained in the mixture which is discharged from the outlet of the fixed-bed reactor is present in an amount maintained at 10 ppm or more.

7. The method of claim 6, wherein the amount of the auxiliary agent added to the feed of glycerol or solvent is controlled such that the auxiliary agent contained in the mixture which is discharged from the outlet of the fixed-bed reactor is present in an amount maintained from 50 ppm to 400 ppm.

8. The method of claim 7, wherein the amount of the auxiliary agent added to the feed of glycerol or solvent is controlled such that the auxiliary agent contained in the mixture which is discharged from the outlet of the fixed-bed reactor is present in an amount maintained from 80 ppm to 300 ppm.

9. The method of claim 1, wherein the noble metal/solid acid catalyst comprises a noble metal selected from one or a combination of platinum, palladium, rhodium, iridium, and ruthenium and a solid acid selected from one or a combination of $ZrO_2$, $WO_3$, $MoO_3$, $Al_2O_3$, $TiO_2$, and $SiO_2$.

10. The method of claim 9, wherein the noble metal in the noble metal/solid acid catalyst is present in an amount of 0.5-3% by weight, and the rest is solid acid.

11. The method of claim 9, wherein the noble metal/solid acid catalyst is Pt—$WO_3$—$ZrO_2$ or Pt—$WO_3$—$Al_2O_3$.

12. The method of claim 1, wherein the reaction temperature is 130-190° C. and the reaction pressure is 1-25 MPa.

13. The method of claim 1, further comprising a solvent in the reaction system selected from water, n-propanol, isopropanol, ethanol, dimethyl sulfoxide, or a combination thereof.

14. The method of claim 13, wherein the solvent in the reaction system includes water.

15. The method of claim 14, wherein the glycerol and water are added in the form of an aqueous glycerol solution, wherein the aqueous glycerol solution has a mass concentration of 20-90% by weight.

16. The method of claim 1, wherein hydrogen to glycerol that is fed into the reaction system is present in a molar ratio from 1:1 to 20:1.

17. A reaction system for preparing 1,3-propanediol by hydrogenolysis of glycerol as used in the method of claim 1, wherein, the reaction system comprises hydrogen, glycerol, a noble metal/solid acid catalyst, and an auxiliary agent wherein the auxiliary agent is selected from an alkali metal phosphate; and wherein the content of the auxiliary agent in a liquid phase of the reaction system is 10 ppm or more.

* * * * *